(12) United States Patent
St. Juste et al.

(10) Patent No.: US 11,511,060 B1
(45) Date of Patent: Nov. 29, 2022

(54) MEDICAL GAS TANK ISOLATION SHROUD WITH UNITARY SLEEVE AND HOOD PORTIONS

(71) Applicants: Martiny St. Juste, Wheatley Heights, NY (US); Burton Brouard, West Babylon, NY (US)

(72) Inventors: Martiny St. Juste, Wheatley Heights, NY (US); Burton Brouard, West Babylon, NY (US)

( * ) Notice: Subject to any disclaimer, the term of this patent is extended or adjusted under 35 U.S.C. 154(b) by 1013 days.

(21) Appl. No.: 16/229,831

(22) Filed: Dec. 21, 2018

(51) Int. Cl.
| | |
|---|---|
| *A61M 16/00* | (2006.01) |
| *A61M 16/08* | (2006.01) |
| *F17C 13/00* | (2006.01) |
| *B65D 65/04* | (2006.01) |
| *B65D 33/28* | (2006.01) |
| *B65D 65/02* | (2006.01) |
| *B65D 65/06* | (2006.01) |
| *B65D 33/16* | (2006.01) |

(Continued)

(52) U.S. Cl.
CPC .... *A61M 16/0003* (2014.02); *A61M 16/0875* (2013.01); *B65D 25/00* (2013.01); *B65D 25/005* (2013.01); *B65D 25/287* (2013.01); *B65D 25/2867* (2013.01); *B65D 29/00* (2013.01); *B65D 29/02* (2013.01); *B65D 33/16* (2013.01); *B65D 33/165* (2013.01); *B65D 33/1608* (2013.01); *B65D 33/1616* (2013.01); *B65D 33/28* (2013.01); *B65D 51/12* (2013.01); *B65D 63/10* (2013.01); *B65D 65/02* (2013.01); *B65D 65/04* (2013.01); *B65D 65/06* (2013.01); *F17C 13/002* (2013.01); *A61M 2202/0208* (2013.01); *A61M 2209/06* (2013.01); *F17C 2201/0119* (2013.01); *F17C 2221/011* (2013.01); *F17C 2270/025* (2013.01)

(58) Field of Classification Search
CPC ...... B65D 20/005; B65D 29/02; B65D 29/00; B65D 51/12; B65D 31/04; B65D 33/16; B65D 33/1608; B65D 33/165; B65D 33/28; B65D 65/06; B65D 65/04; B65D 65/02; F17C 13/002
USPC ..... 220/737, 903; 150/165, 154; 383/99, 98, 383/80, 78, 62, 42
See application file for complete search history.

(56) References Cited

U.S. PATENT DOCUMENTS

| | | |
|---|---|---|
| 1,395,485 A | 11/1921 | Duncan et al. |
| 2,078,400 A | 4/1937 | Maupin |

(Continued)

*Primary Examiner* — Robert J Hicks
(74) *Attorney, Agent, or Firm* — Goldstein Law Offices, P.C.

(57) ABSTRACT

An isolation shroud adapted to enclose and protect a medical gas tank against contamination, which is further replaceable between patients to prevent cross-contamination, comprising a sleeve portion with an open end and interior space, and a hood portion with a hood lower opening, adapted to enclose the body and upper end of the medical gas tank respectively. The hood portion is attached to and is continuous with a sleeve order surrounding the open end of the sleeve portion, allowing the open end and sleeve border to be simultaneously lifted to enclose the body and open end respectively. The hood portion further has a hood front opening, allowing a hose to extend from the medical gas tank outwardly through either the hood lower opening or front opening. A fastener attached to the hood portion further allows the hood lower opening to be sealed against the sleeve portion.

8 Claims, 3 Drawing Sheets

(51) Int. Cl.
*B65D 25/00* (2006.01)
*B65D 25/28* (2006.01)
*B65D 51/12* (2006.01)
*B65D 30/00* (2006.01)
*B65D 30/08* (2006.01)
*B65D 63/10* (2006.01)

(56) References Cited

U.S. PATENT DOCUMENTS

| | | | |
|---|---|---|---|
| 2,838,085 A * | 6/1958 | Beeler | B23B 5/16 |
| | | | 190/115 |
| 4,022,343 A * | 5/1977 | Richardson | B65D 59/06 |
| | | | 206/521 |
| 4,109,692 A | 8/1978 | Brown | |
| 4,383,528 A * | 5/1983 | Eppolito | A62B 9/04 |
| | | | 224/259 |
| 4,438,764 A * | 3/1984 | Eppolito | A62B 9/04 |
| | | | 224/259 |
| 4,967,923 A | 11/1990 | Wren | |
| 6,508,282 B2 | 1/2003 | Garofalo et al. | |
| D517,162 S | 3/2006 | Clower | |
| 7,753,589 B2 | 7/2010 | Palt | |
| 2005/0194266 A1 | 9/2005 | Peterolff et al. | |
| 2008/0050051 A1* | 2/2008 | Palt | F17C 13/084 |
| | | | 383/41 |
| 2008/0073355 A1* | 3/2008 | Akbar | B65D 33/14 |
| | | | 220/562 |

\* cited by examiner

MEDICAL GAS TANK ISOLATION SHROUD WITH UNITARY SLEEVE AND HOOD PORTIONS

TECHNICAL FIELD

The present disclosure relates generally to a protective cover for a medical gas tank. More particularly, the present disclosure relates to a medical gas tank isolation shroud with a unitary sleeve and hood portions.

BACKGROUND

Controlling the spread of infectious disease is a major goal in hospital, nursing home, and other healthcare settings. Wiping down and disinfecting used medical equipment, the practice of hand washing, and the use of gloves and gowns by medical staff and caregivers are all measures designed to achieve this goal. However, in certain cases, wiping down medical equipment proves to be too time consuming or inefficient. For example, patients who are being transported between facilities or within a particular facility, frequently require oxygen supplied via an oxygen tank. The oxygen tank is often placed on the patient's stretcher or bed, where it comes into contact with pathogens, as well as soiled bedding. As these tanks are generally bulky and heavy, it is not feasible to prepare a fresh oxygen tank for each new patient, and oxygen tanks therefore remain in use until depleted. However oxygen tanks must be thoroughly cleaned in order to prevent cross-contamination between successive patients.

As an alternative to cleaning the oxygen tank between patients, various devices exist in the prior art, which are designed to enclose and protect the gas tanks from contact with contaminants. These devices often employ zippers, laces, and/or a complex arrangement of overlapping flaps to enclose the tank. Many of these devices do not fully enclose the gas tank and are therefore of little use in preventing cross-contamination from pathogens, while other more protective devices are comprised of multiple components which require assembly or adjustment, making them unsuitable for rapid removal and replacement in emergency situations where the patient must be provided with oxygen as quickly as possible.

An urgent need therefore exists for an isolation shroud which not only fully encloses a medical gas tank to protect it against contamination, but which is also unitary to facilitate rapid and efficient removal and replacement, allowing the medical gas tank to deliver gas to successive patients without cross-contamination.

While these units may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a unitary isolation shroud for protecting a medical gas tank from contaminants, the medical gas tank having a body with a lower and an upper end, a gas outlet and valve, and a hose selectively attached to the gas outlet. Accordingly, the present disclosure provides an isolation shroud having a sleeve portion with a closed end and an open end adapted to enclose the body of the medical gas tank, and a hood portion having a hood lower opening which is continuous with the sleeve portion and is adapted to enclose the upper end of the body along with the gas outlet and valve, thus forming a barrier against contaminants that encloses and protects the entirety of the medical gas tank.

It is another aspect of an example embodiment in the present disclosure to provide a unitary isolation shroud which allows the hose to extend outwardly from the hood portion to deliver gas for medical use. Accordingly, the hood portion further has a hood front opening in addition to the hood lower opening, and is adapted to allow the hose to project through either the hood front opening or the hood lower opening.

It is yet another aspect of an example embodiment in the present disclosure to provide a unitary isolation shroud which is sealed between the hood portion and the sleeve portion. Accordingly, the present disclosure provides a fastening means attached to the hood portion adapted to tighten the hood lower opening against the sleeve portion, as well as draw together the hood front opening to form overlapping flaps.

It is a further aspect of an example embodiment in the present disclosure to provide a unitary isolation shroud which allows the medical gas tank to be used with multiple successive patients without cross-contamination of pathogens. Accordingly, the unitary isolation shroud is adapted to be removed and replaced prior to using the medical gas tank with the next patient, and the continuous arrangement between the sleeve portion and the hood portion ensures that the sleeve portion and the hood portion are lifted upwardly simultaneously to enclose the body of the medical gas tank and position the hood portion proximate to the upper end, reducing the time required before gas is delivered to the next patient.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 1:
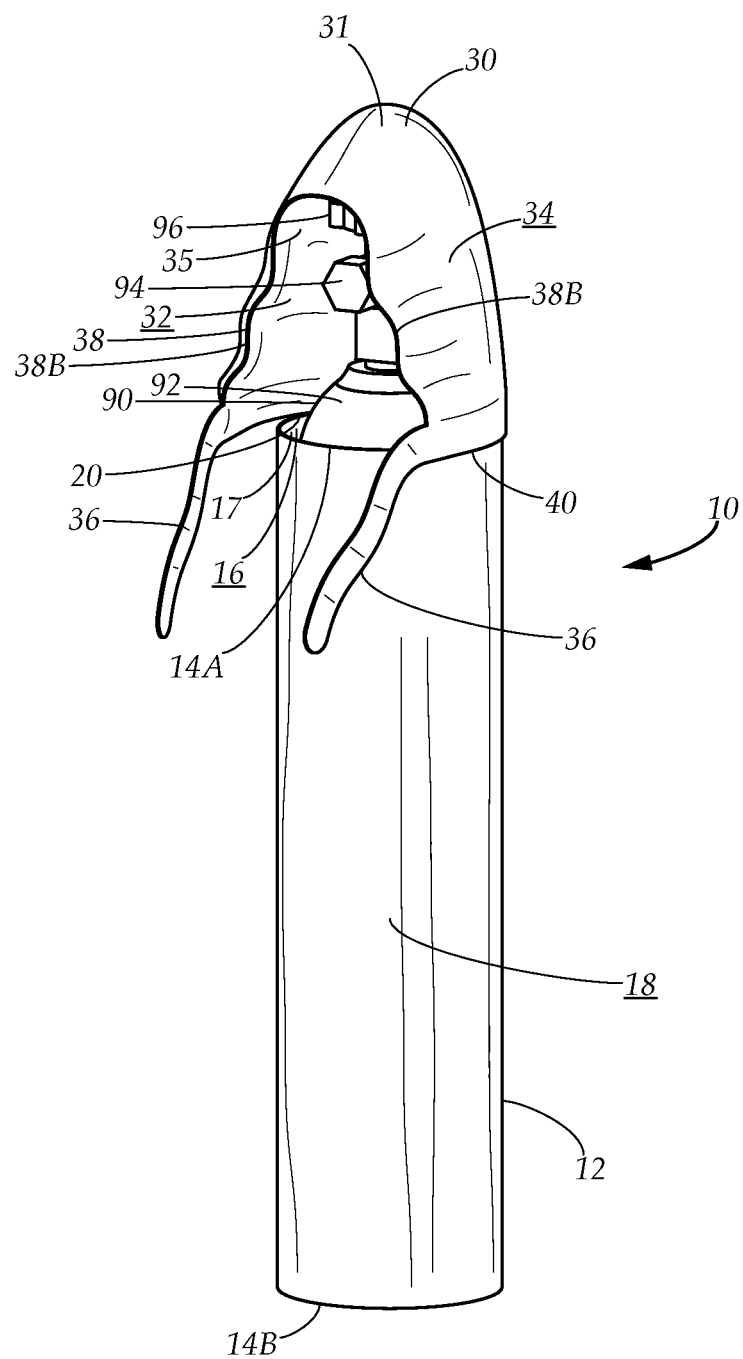
FIG. 1 is a diagrammatical perspective view depicting an isolation shroud with unitary sleeve and hood portions. The sleeve portion is shown enclosing a medical gas tank, and a hood portion is shown covering the gas outlet and valve of the medical gas tank, in accordance with an embodiment of the present disclosure.
Figure 2:
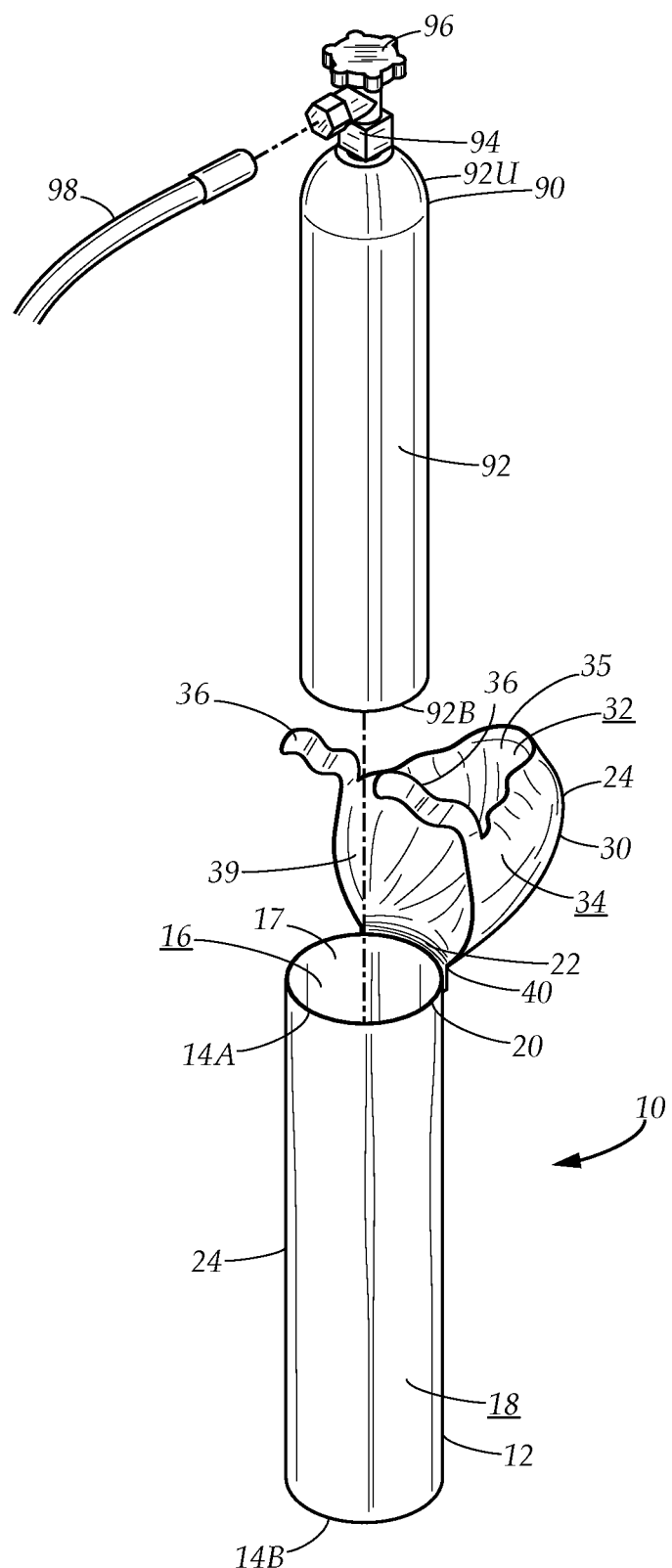
FIG. 2 is a diagrammatical exploded view of the isolation shroud with the medical gas tank removed, depicting the sleeve portion with an interior space adapted to receive the medical gas tank, and a connecting flap which joins the hood portion to the sleeve portion, in accordance with an embodiment of the present disclosure.

FIG. 1 illustrates an isolation shroud 10 comprising a unitary sleeve portion 12 and hood portion 30, which is adapted to enclose and isolate a medical gas tank 90, forming a barrier against contamination from pathogens via the air or through direct contact. The medical gas tank 90 has a body 92 which is typically elongated and cylindrical in shape, which contains gas used in a healthcare setting, such as oxygen. The medical gas tank 90 further has a gas outlet 94 and a valve 96 for controllably releasing the gas contained therein. Referring to FIG. 2, the body 92 has a bottom end 92B, and a distally oriented upper end 92U, where the gas outlet 94 and valve 96 are located. The gas outlet 94 is adapted to connect to a gas hose 98, and the gas may be selectively released through the gas hose 98 using the valve 96. The medical gas tank 90 may be placed on a bed or stretcher to deliver gas to a patient, and the isolation shroud 10 is further adapted to prevent exposure to contamination of the medical gas tank 90 from contact with soiled bedding material.

Continuing to refer to FIGS. 1-2, the sleeve portion 12 and hood portion 30 of the isolation shroud 10 are fashioned from one or more sheets 24 of polyethylene plastic, natural or synthetic cloth, fibers, or other light flexible material, in one or more layers as required to achieve desired properties such as resilience and/or impermeability. To achieve the unitary character of the isolation shroud 10, the hood portion 30 and the sleeve portion 12 may be fashioned continuously using the same sheet 24, or may alternatively be contiguously attached together using more than one sheet 24.

In a preferred embodiment, the sleeve portion 12 is adapted to receive and enclose the body 92 of the medical gas tank 90 and is substantially cylindrical in shape. The sleeve portion 12 has an open end 14A, a distally oriented closed end 14B, and an inner surface 16 and an outer surface 18 disposed therebetween. The open end 14A is adapted to allow the body 92 of the medical gas tank 90 to pass therethrough. The sleeve portion 12 further has an interior space 17 which receives the body 92 and is defined by the inner surface 16, the closed end 14B, and the open end 14A. The sleeve portion 12 may further have a sleeve border 20 which is coextensive with the circumference of the open end 14A.

The hood portion 30 has a hood top 31, a hood outer surface 34, and a hood inner surface 32 defining a hood concavity 35 and a hood lower opening 39 which opens downwardly away from the hood top 31 when the hood is in a raised position. The hood portion 30 further has a hood lower border 40 which surrounds the hood lower opening 39. The hood portion 30 may also have a hood front opening 38, surrounded by a front opening border 38B. The hood front opening 38 extends upwardly from the hood lower border 40 towards the hood top 31. In a preferred embodiment, the hood lower border 40 does not have a continuous circumference but is divided by the hood front opening 38. The hood portion 30 further has a pair of fastening straps 36 attached to the hood lower border 40, on opposite sides of the hood front opening 38. In a preferred embodiment, the hood lower border 40 is partially continuous with the sleeve border 20, forming a connecting flap 22 opposite the hood front opening 38 which joins the sleeve portion 12 to the hood portion 30. The connecting flap 22 may be unitary with the sleeve and hood portions 12, 30. However, in alternate embodiments, the connecting flap 22 may instead be a separate piece which is sewn, glued, or otherwise attached to the sleeve and hood portions 12, 30. The unitary arrangement of the hood and sleeve portions 30, 12 ensures the hood portion 30 is always attached to the sleeve border 20 is and ready to be raised, and further prevents the hood portion 30 from becoming unintentionally detached from the sleeve portion 12 when subjected to contact such as jostling, or rough handling. This feature crucially shortens the time required to prepare the medical gas tank 90 for use with the next patient as there is no need to locate and attach a separate hood.

When not in the raised position, the hood portion 30 hangs freely along the connecting flap 22. In an alternate embodiment, the hood front opening 38 is not present on the hood portion 30 and the circumference of the hood lower border 40 may be continuous around the hood lower opening 39.

In order to employ the isolation shroud 10, the bottom end 92B of the body 92 is inserted through the open end 14A, until the bottom end 92B contacts the closed end 14B of the sleeve portion. The sleeve border 20 surrounding the open end 14A is then lifted upwardly until it is proximate to the upper end 92U of the body 92 and below the gas outlet 94. To enclose the upper end 92U of the body, the hood portion 30 is raised upwardly and then lowered such that the upper end 92U passes through the hood lower opening 39 and is contained within the hood concavity 35, along with the gas outlet 94 and valve 96. The hood concavity 35 contains sufficient vertical space between the hood lower border 40 and the hood top 31 to enclose and contain the gas outlet 94 and valve 96, to enable the hood lower border 40 to overlap the sleeve portion 12 below the sleeve border 20 when the hood portion 30 is in the raised position, thus preventing any gap from forming between the hood portion 30 and the sleeve portion 12.

Figure 3:
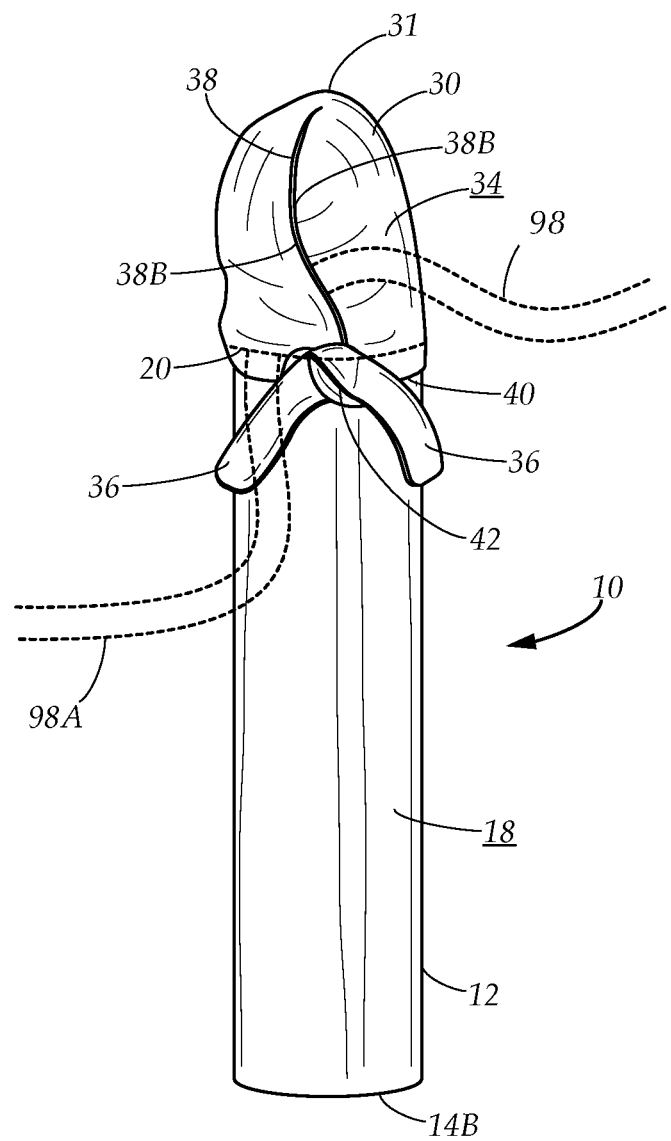
FIG. 3 is a diagrammatical perspective view of the isolation shroud where the hood portion is raised and secured and the medical gas tank is fully enclosed, in accordance with an embodiment of the present disclosure.

Turning to FIG. 3 while continuing to refer to FIGS. 1-2, the fastening straps 36 are secured together, causing the hood lower border 40 to tighten around the medical gas tank 90 below the sleeve border 20, creating a seal which results in the medical gas tank 90 being entirely enclosed by the isolation shroud 10. The optimum position for securing the fastening straps 36 may vary according to the medical gas tank 90 being used. In certain embodiments, the sleeve border 20 may extend upwardly past the upper end 92U of the body to partially overlap the gas outlet 94. As the hood lower border 40 extends downwardly past the sleeve border 20, the fastening straps 36 may be secured anywhere between the gas outlet 94 and the upper end 92U of the body 92 so long as the hood lower border 40 overlaps the outer surface 18 of the sleeve portion 12 past the sleeve border 20.

The fastening straps 36 may alternatively be secured around the body 92. Securing the fastening straps 36 also causes the hood front opening 38 to close by drawing together the front opening border 38B to form overlapping flaps. In a preferred embodiment, the fastening straps 36 can be secured by tying the fastening straps 36 to form a knot 42, although other fastening means, such as hook and loop fasteners, drawstrings, and other means, may be employed in alternative embodiments.

The hose 98 may be connected to the gas outlet 94 at any time before the hood portion 30 is placed in the raised position. Once the hood portion 30 is in the raised position and the hood lower border 40 is tightened, the hose 98 may protrude downwardly 98A between the hood lower border 40 and the sleeve border 20 of the sleeve portion 12. Tightening the fastening straps 36 causes the hood lower border 40 to wrap around the hose 98 to preserve the seal between the hood lower border 40 and the outer surface 18 of the sleeve portion 12, ensuring that the medical gas tank 90 remains protected against direct external contact even as the hose 98 passes therebetween. Where the hood front opening 38 is present in an embodiment, the hose 98 may alternatively pass through the hood front opening 38 between the overlapping flaps of the front opening border 38B. Due to the flexible nature of the hood portion 30, the valve 96 may be manipulated by hand through the hood outer surface 34 while the hood portion 30 is in the raised position, allowing the flow of the gas to be controlled without exposing the medical gas tank 90 to contamination.

As the medical gas tank 90 may be used to deliver gas to a succession of different patients until the gas stored within is depleted, cross-contamination and the spread of diseases and infection between the patients is prevented by removal and replacement of the isolation shroud 10 prior to utilizing the medical gas tank 90 to treat the next patient. Referring to FIGS. 3 and 2, the knot 42 is undone and the fastening straps 36 are loosened to allow the hood portion 30 to be lifted to uncover the upper end 92U of the medical gas tank 90. The body 92 of the medical gas tank 90 may then be removed from the interior space 17 of the sleeve portion 12 by pulling the sleeve portion 12 downward, and lifting the body 92 upwardly until the bottom end 92B passes through the open end 14A of the sleeve portion 12. The medical gas tank 90 does not contact the outer surface 18 of the sleeve portion 12 or the hood outer surface 34 while the isolation shroud 10 is removed, and remains free of contaminants. If necessary, the hose 98 may be detached from the gas outlet 94 and replaced with a new hose 98. Once the medical gas tank 90 is placed within a new isolation shroud 10, it is ready for use with the next patient. In a preferred embodiment, the isolation shroud 10 is disposable, and may simply be discarded once the outer surfaces 18, 34 become contaminated.

Note that the isolation shroud 10 may be modified for use with medical gas tanks of varying shapes and sizes, and a person of ordinary skill in the art in the field of the invention will appreciate that the dimensions and proportions of the hood and sleeve portions 30, 12 may be adjusted appropriately in adherence with the principles of the present disclosure. Furthermore, the features of the isolation shroud 10 may be adapted for use with gas tanks other than medical gas tanks. For example, the isolation shroud 10 may be adapted to protect fuel gas cylinders from exposure to the environmental damage and corrosion.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a medical gas tank isolation shroud with unitary hood and sleeve portions. The disclosure is illustrated by example in the drawing figures, and throughout the written description. It should be understood that numerous variations are possible, while adhering to the inventive concept. Such variations are contemplated as being a part of the present disclosure.

What is claimed is:

1. An isolation shroud for protecting a medical gas tank against contaminants, the medical gas tank is adapted to store gas and has a body with a bottom end, a distally oriented upper end, and a gas outlet and valve disposed on the upper end for controllably releasing the gas through a selectively attachable hose to be administered to a patient, the isolation shroud comprising:
  a sleeve portion having a closed end, a distally oriented open end, an outer surface, an inner surface, and an interior space defined by the inner surface, the open end, and the closed end, the open end is surrounded by a sleeve border and is adapted to allow the bottom end of the medical gas tank to be inserted therein, and the interior space is adapted to receive and enclose the body of the medical gas tank, allowing the sleeve portion to protect the body against contact with the contaminants;
  a hood portion having a hood top, a hood outer surface, a hood inner surface, a hood concavity formed by the hood inner surface, and a hood lower opening oriented downwardly away from the hood top, the hood lower opening is surrounded by a hood lower border;
  a connecting flap which both joins and is continuous with the sleeve portion and the hood portion, the connection flap corresponds to a portion of the hood lower border which is partially continuous with the sleeve border, the connecting flap is adapted to allow the hood portion to be raised about the connecting flap to a raised position over the upper end of the body such that the upper end passes through the hood lower opening to be contained within the hood concavity, wherein the hood lower border is adapted to overlap the outer surface of the sleeve portion below the sleeve border when the hood portion is in the raised position, allowing the hood portion to enclose and protect the upper end against contact with the contaminants, such that the combination of the hood portion and the sleeve portion is adapted to fully enclose the medical gas tank;
  a securable fastening means attached to the hood lower border adapted to tighten the hood lower opening against the sleeve portion and the body of the medical gas tank when the hood portion is in the raised position; and
  wherein the hood portion further has a hood front opening which opens forwardly when the hood portion is in the raised position, the hood front opening extends from the hood lower border upwardly toward the hood top, and the hood front opening is adapted to allow the hose to exit the hood concavity by extending downwardly through the hood front opening and between the hood lower border and the outer surface of the sleeve portion.

2. The isolation shroud as described in claim 1, wherein the hood front opening is surrounded by a hood front border, and whereby securing the fastening means causes the hood front border to draw together to form overlapping flaps.

3. The isolation shroud as described in claim 2, wherein the fastening means correspond to a pair of fastening straps which are secured by being tied to form a knot.

4. A method for administering a gas to a patient using a medical gas tank while protecting the medical gas tank against contaminants, the medical gas tank is adapted to store gas and has a body with a bottom end, a distally oriented upper end, and a gas outlet and valve disposed on the upper end for controllably releasing the gas through a selectively attachable hose, the method comprising the steps of:
  providing an isolation shroud having:
    a sleeve portion having a closed end, a distally oriented open end adapted to allow the bottom end of the medical gas tank to be inserted therethrough, an inner surface and an outer surface, and an interior space adapted to receive and enclose the body of the medical gas tank, the sleeve portion further having a sleeve border which surrounds the open end;
    a hood portion having a hood top, a hood inner surface and hood outer surface, a hood lower opening, a hood lower border which surrounds the hood lower opening, and a hood concavity formed by the hood inner surface between the hood lower opening and the hood top; and
    a connecting flap which both joins and is continuous with the hood portion and the sleeve portion;
  inserting the bottom end of the medical gas tank through the open end of the sleeve portion;
  lifting the sleeve border, connecting flap, and hood portion simultaneously until the body of the medical gas tank is enclosed within the interior space;
  raising the hood portion about the connecting flap and lowering the hood lower opening over the upper end, gas outlet, and valve of the medical gas tank until the hood lower border overlaps the outer surface of the sleeve portion below the sleeve border;
  forming a protective barrier against contamination whereby the medical gas tank is fully enclosed by the sleeve portion and the hood portion;
  administering the gas to the patient using the hose;
  uncovering the upper end of the medical gas tank, and removing the medical gas tank from the interior space of sleeve portion; and
  replacing the isolation shroud with a new isolation shroud, enclosing the medical gas tank using the new isolation shroud, and administering the gas to a new patient.

5. The method as described in claim 4, wherein:
the hood portion further has a fastening means attached to the hood lower border adapted to tighten the lower hood opening; and
the step of raising the hood portion is followed by the step of:
  securing the fastening means and tightening the hood lower opening, and sealing the hood lower border against the outer surface of the sleeve portion.

6. The method as described in claim 5, wherein:
the step of raising the hood portion further comprises the step of positioning the hose to exit the hood concavity and extend downwardly between the hood lower border and the sleeve outer surface; and
the step of securing the fastening means and tightening the hood lower opening further comprises the step of sealing the hood lower border against the outer surface of the sleeve portion with the hose positioned therebetween.

7. The method as described in claim 5, wherein:
the hood portion further has a hood front opening, and the fastening means is further adapted to tighten the hood front opening; and
the step of securing the fastening means further comprises the step of sealing the hood front opening.

8. The method as described in claim 7, wherein:
the hood front opening is surrounded by a front opening border;
the step of raising the hood portion further comprises the step of positioning the hose to exit the hood concavity forwardly through the hood front opening; and
the step of securing the fastening means further comprises the steps of sealing the hood front opening by drawing the front opening border together, and forming overlapping flaps to seal the hose therebetween.

* * * * *